US012648717B2

(12) United States Patent

Hayter et al.

(10) Patent No.: US 12,648,717 B2

(45) Date of Patent: Jun. 9, 2026

(54) METHODS, DEVICES AND SYSTEM FOR PROVIDING DIABETIC CONDITION DIAGNOSIS AND THERAPY

(71) Applicant: ABBOTT DIABETES CARE INC., Alameda, CA (US)

(72) Inventors: Gary Alan Hayter, Oakland, CA (US); Daniel Milfred Bernstein, El Granada, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 346 days.

(21) Appl. No.: 18/117,699

(22) Filed: Mar. 6, 2023

(65) Prior Publication Data

US 2023/0200687 A1  Jun. 29, 2023

Related U.S. Application Data

(63) Continuation of application No. 15/926,919, filed on Mar. 20, 2018, now Pat. No. 11,596,330.

(60) Provisional application No. 62/474,605, filed on Mar. 21, 2017.

(51) Int. Cl.
| | |
|---|---|
| *A61B 5/145* | (2006.01) |
| *A61B 5/00* | (2006.01) |
| *A61B 5/1486* | (2006.01) |

(52) U.S. Cl.
CPC ........ *A61B 5/14532* (2013.01); *A61B 5/0004* (2013.01); *A61B 5/1451* (2013.01); *A61B 5/1486* (2013.01); *A61B 5/4848* (2013.01); *A61B 5/4866* (2013.01)

(58) Field of Classification Search
CPC . A61B 5/14532; A61B 5/0004; A61B 5/1451; A61B 5/1486; A61B 5/4848; A61B 5/4866; G16H 50/20; G16H 50/30
See application file for complete search history.

(56) References Cited

U.S. PATENT DOCUMENTS

| | | | |
|---|---|---|---|
| 3,581,062 | A | 5/1971 | Aston |
| 3,926,760 | A | 12/1975 | Allen et al. |
| 3,949,388 | A | 4/1976 | Fuller |
| 3,960,497 | A | 6/1976 | Acord et al. |
| 4,033,330 | A | 7/1977 | Willis et al. |

(Continued)

FOREIGN PATENT DOCUMENTS

| | | |
|---|---|---|
| EP | 0098592 | 1/1984 |
| EP | 0127958 | 12/1984 |

(Continued)

OTHER PUBLICATIONS

Boyne, M. S., et al., Timing of Changes in Interstitial and Venous Blood Glucose Measured With a Continuous Subcutaneous Glucose Sensor, Diabetes, vol. 52, Nov. 2003, pp. 2790-2794. (Year: 2003).*

(Continued)

*Primary Examiner* — Linh Giang Le

(74) *Attorney, Agent, or Firm* — Sterne, Kessler, Goldstein & Fox P.L.L.C.

(57) ABSTRACT

Methods, devices and system for determining fasting glucose level information and post-prandial glucose level information for diagnosing pre-diabetic and diabetic conditions based on monitored glucose measurements are provided.

17 Claims, 7 Drawing Sheets

100

(56)                    References Cited

U.S. PATENT DOCUMENTS

| | | |
|---|---|---|
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,243,696 A | 9/1993 | Carr et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |

(56) References Cited

U.S. PATENT DOCUMENTS

| | | | |
|---|---|---|---|
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,871 A | 11/2000 | Saito et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,025 B1 | 5/2004 | Platt |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |

(56)                    References Cited

U.S. PATENT DOCUMENTS

| | | | |
|---|---|---|---|
| 7,003,340 | B2 | 2/2006 | Say et al. |
| 7,003,341 | B2 | 2/2006 | Say et al. |
| 7,009,511 | B2 | 3/2006 | Mazar et al. |
| 7,011,630 | B2 | 3/2006 | Desai et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,072 | B2 | 4/2006 | Fox et al. |
| 7,022,219 | B2 | 4/2006 | Mansouri et al. |
| 7,024,236 | B2 | 4/2006 | Ford et al. |
| 7,024,245 | B2 | 4/2006 | Lebel et al. |
| 7,025,425 | B2 | 4/2006 | Kovatchev et al. |
| 7,027,848 | B2 | 4/2006 | Robinson et al. |
| 7,027,931 | B1 | 4/2006 | Jones et al. |
| 7,029,444 | B2 | 4/2006 | Shin et al. |
| 7,041,068 | B2 | 5/2006 | Freeman et al. |
| 7,041,468 | B2 | 5/2006 | Drucker et al. |
| 7,043,305 | B2 | 5/2006 | KenKnight et al. |
| 7,046,153 | B2 | 5/2006 | Oja et al. |
| 7,052,472 | B1 | 5/2006 | Miller et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,092,891 | B2 | 8/2006 | Maus et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,123,950 | B2 | 10/2006 | Mannheimer |
| 7,125,382 | B2 | 10/2006 | Zhou et al. |
| 7,134,999 | B2 | 11/2006 | Brauker et al. |
| 7,136,689 | B2 | 11/2006 | Shults et al. |
| 7,153,265 | B2 | 12/2006 | Vachon |
| 7,155,290 | B2 | 12/2006 | Von Arx et al. |
| 7,167,818 | B2 | 1/2007 | Brown |
| 7,171,274 | B2 | 1/2007 | Starkweather et al. |
| 7,174,199 | B2 | 2/2007 | Berner et al. |
| 7,179,226 | B2 | 2/2007 | Crothall et al. |
| 7,183,102 | B2 | 2/2007 | Monfre et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,225,535 | B2 | 6/2007 | Feldman et al. |
| 7,226,442 | B2 | 6/2007 | Sheppard et al. |
| 7,226,978 | B2 | 6/2007 | Tapsak et al. |
| 7,228,182 | B2 | 6/2007 | Healy et al. |
| 7,237,712 | B2 | 7/2007 | DeRocco et al. |
| 7,258,673 | B2 | 8/2007 | Racchini et al. |
| 7,267,665 | B2 | 9/2007 | Steil et al. |
| 7,276,029 | B2 | 10/2007 | Goode, Jr. et al. |
| 7,278,983 | B2 | 10/2007 | Ireland et al. |
| 7,286,894 | B1 | 10/2007 | Grant et al. |
| 7,295,867 | B2 | 11/2007 | Berner et al. |
| 7,299,082 | B2 | 11/2007 | Feldman et al. |
| 7,310,544 | B2 | 12/2007 | Brister et al. |
| 7,317,938 | B2 | 1/2008 | Lorenz et al. |
| 7,318,816 | B2 | 1/2008 | Bobroff et al. |
| 7,324,850 | B2 | 1/2008 | Persen et al. |
| 7,335,294 | B2 | 2/2008 | Heller et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,384,397 | B2 | 6/2008 | Zhang et al. |
| 7,387,010 | B2 | 6/2008 | Sunshine et al. |
| 7,399,277 | B2 | 7/2008 | Saidara et al. |
| 7,402,153 | B2 | 7/2008 | Steil et al. |
| 7,404,796 | B2 | 7/2008 | Ginsberg |
| 7,419,573 | B2 | 9/2008 | Gundel |
| 7,424,318 | B2 | 9/2008 | Brister et al. |
| 7,460,898 | B2 | 12/2008 | Brister et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,474,992 | B2 | 1/2009 | Ariyur |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,519,408 | B2 | 4/2009 | Rasdal et al. |
| 7,519,478 | B2 | 4/2009 | Bartkowiak et al. |
| 7,523,004 | B2 | 4/2009 | Bartkowiak et al. |
| 7,547,281 | B2 | 6/2009 | Hayes et al. |
| 7,565,197 | B2 | 7/2009 | Haubrich et al. |
| 7,569,030 | B2 | 8/2009 | Lebel et al. |
| 7,574,266 | B2 | 8/2009 | Dudding et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,630,748 | B2 | 12/2009 | Budiman |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |
| 7,651,596 | B2 | 1/2010 | Petisce et al. |
| 7,651,845 | B2 | 1/2010 | Doyle, III et al. |
| 7,653,425 | B2 | 1/2010 | Hayter et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,668,596 | B2 | 2/2010 | Von Arx et al. |
| 7,699,775 | B2 | 4/2010 | Desai et al. |
| 7,699,964 | B2 | 4/2010 | Feldman et al. |
| 7,711,402 | B2 | 5/2010 | Shults et al. |
| 7,711,493 | B2 | 5/2010 | Bartkowiak et al. |
| 7,713,574 | B2 | 5/2010 | Brister et al. |
| 7,715,893 | B2 | 5/2010 | Kamath et al. |
| 7,736,310 | B2 | 6/2010 | Taub et al. |
| 7,741,734 | B2 | 6/2010 | Joannopoulos et al. |
| 7,751,864 | B2 | 7/2010 | Buck, Jr. |
| 7,766,829 | B2 | 8/2010 | Sloan et al. |
| 7,768,386 | B2 | 8/2010 | Hayter et al. |
| 7,768,387 | B2 | 8/2010 | Fennell et al. |
| 7,771,352 | B2 | 8/2010 | Shults et al. |
| 7,774,145 | B2 | 8/2010 | Brauker et al. |
| 7,775,444 | B2 | 8/2010 | DeRocco et al. |
| 7,778,680 | B2 | 8/2010 | Goode et al. |
| 7,779,332 | B2 | 8/2010 | Karr et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,811,231 | B2 | 10/2010 | Jin et al. |
| 7,813,809 | B2 | 10/2010 | Strother et al. |
| 7,826,382 | B2 | 11/2010 | Sicurello et al. |
| 7,826,981 | B2 | 11/2010 | Goode, Jr. et al. |
| 7,831,310 | B2 | 11/2010 | Lebel et al. |
| 7,857,760 | B2 | 12/2010 | Brister et al. |
| 7,860,574 | B2 | 12/2010 | Von Arx et al. |
| 7,882,611 | B2 | 2/2011 | Shah et al. |
| 7,885,697 | B2 | 2/2011 | Brister et al. |
| 7,889,069 | B2 | 2/2011 | Fifolt et al. |
| 7,899,511 | B2 | 3/2011 | Shults et al. |
| 7,899,545 | B2 | 3/2011 | John |
| 7,905,833 | B2 | 3/2011 | Brister et al. |
| 7,912,674 | B2 | 3/2011 | Killoren Clark et al. |
| 7,914,450 | B2 | 3/2011 | Goode, Jr. et al. |
| 7,916,013 | B2 | 3/2011 | Stevenson |
| 7,920,906 | B2 | 4/2011 | Goode et al. |
| 7,928,850 | B2 | 4/2011 | Hayter et al. |
| 7,938,797 | B2 | 5/2011 | Estes |
| 7,941,200 | B2 | 5/2011 | Weinert et al. |

(56) References Cited

U.S. PATENT DOCUMENTS

| | | | |
|---|---|---|---|
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,996,158 B2 | 8/2011 | Hayter et al. |
| 7,999,674 B2 | 8/2011 | Kamen |
| 8,005,524 B2 | 8/2011 | Brauker et al. |
| 8,010,174 B2 | 8/2011 | Goode et al. |
| 8,010,256 B2 | 8/2011 | Oowada |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,409,093 B2 | 4/2013 | Bugler |
| 8,444,560 B2 | 5/2013 | Hayter et al. |
| 8,461,985 B2 | 6/2013 | Fennell et al. |
| 8,478,557 B2 | 7/2013 | Hayter et al. |
| 8,484,005 B2 | 7/2013 | Hayter et al. |
| 8,543,354 B2 | 9/2013 | Luo et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,657,746 B2 | 2/2014 | Roy |
| 8,682,615 B2 | 3/2014 | Hayter et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 8,954,373 B2 | 2/2015 | Atlas et al. |
| 9,060,719 B2 | 6/2015 | Hayter et al. |
| 9,289,179 B2 | 3/2016 | Hayter et al. |
| 9,398,872 B2 | 7/2016 | Hayter et al. |
| 9,408,566 B2 | 8/2016 | Hayter et al. |
| 9,439,586 B2 | 9/2016 | Bugler |
| 9,483,608 B2 | 11/2016 | Hayter et al. |
| 9,558,325 B2 | 1/2017 | Hayter et al. |
| 9,743,872 B2 | 8/2017 | Hayter et al. |
| 2001/0037366 A1 | 11/2001 | Webb et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0150959 A1 | 10/2002 | Lejeunne et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0034289 A1 | 2/2004 | Teller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0111017 A1 | 6/2004 | Say et al. |

(56)     References Cited

U.S. PATENT DOCUMENTS

| | | |
|---|---|---|
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0162678 A1 | 8/2004 | Hetzel et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |

(56) References Cited

U.S. PATENT DOCUMENTS

| | | |
|---|---|---|
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0151869 A1 | 7/2007 | Heller et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |

(56) References Cited

U.S. PATENT DOCUMENTS

| | | |
|---|---|---|
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |

(56)  References Cited

U.S. PATENT DOCUMENTS

| | | |
|---|---|---|
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0064764 A1 | 3/2010 | Hayter et al. |
| 2010/0075353 A1 | 3/2010 | Heaton |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094111 A1 | 4/2010 | Heller et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213080 A1 | 8/2010 | Celentano et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0261987 A1 | 10/2010 | Kamath et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0312176 A1 | 12/2010 | Lauer et al. |
| 2010/0313105 A1 | 12/2010 | Nekoomaram et al. |
| 2010/0332445 A1 | 12/2010 | Ray et al. |
| 2011/0004085 A1 | 1/2011 | Mensinger et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0213225 A1 | 9/2011 | Bernstein et al. |
| 2011/0257895 A1 | 10/2011 | Brauker et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2011/0320167 A1 | 12/2011 | Budiman |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0138484 A1 | 6/2012 | Bommakanti et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0186997 A1* | 7/2012 | Li ........................... C12Q 1/005 |
| | | 204/403.14 |
| 2012/0190989 A1 | 7/2012 | Kaiser et al. |
| 2012/0245447 A1 | 9/2012 | Karan et al. |
| 2013/0035575 A1 | 2/2013 | Mayou et al. |
| 2013/0184547 A1 | 7/2013 | Taub et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0245547 A1 | 9/2013 | El-Khatib et al. |
| 2013/0324823 A1 | 12/2013 | Koski et al. |
| 2014/0005499 A1 | 1/2014 | Catt et al. |
| 2014/0024907 A1 | 1/2014 | Howell et al. |
| 2014/0046160 A1 | 2/2014 | Terashima et al. |
| 2014/0058237 A1 | 2/2014 | Galley et al. |
| 2014/0121480 A1 | 5/2014 | Budiman et al. |
| 2014/0121488 A1 | 5/2014 | Budiman |
| 2015/0216456 A1 | 8/2015 | Budiman |
| 2015/0241407 A1 | 8/2015 | Ou et al. |
| 2016/0022221 A1 | 1/2016 | Ou et al. |
| 2016/0256087 A1* | 9/2016 | Doyle, III .............. A61B 5/725 |
| 2017/0053084 A1 | 2/2017 | McMahon et al. |
| 2017/0185748 A1* | 6/2017 | Budiman ............. A61B 5/7282 |
| 2017/0296746 A1 | 10/2017 | Chen et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 3043174 | 7/2016 |
| WO | WO-1993/006237 | 4/1993 |
| WO | WO-1996/025089 | 8/1996 |
| WO | WO-1996/035370 | 11/1996 |
| WO | WO-2000/049940 | 8/2000 |
| WO | WO-2000/059370 | 10/2000 |
| WO | WO-2001/052935 | 7/2001 |
| WO | WO-2001/054753 | 8/2001 |
| WO | WO-2002/016905 | 2/2002 |
| WO | WO-2003/076893 | 9/2003 |
| WO | WO-2003/082091 | 10/2003 |
| WO | WO-2004/047445 | 6/2004 |
| WO | WO-2005/010756 | 2/2005 |
| WO | WO-2005/040404 | 5/2005 |
| WO | WO-2006/024671 | 3/2006 |
| WO | WO-2006/051466 | 5/2006 |
| WO | WO-2006/064397 | 6/2006 |
| WO | WO-2007/007459 | 1/2007 |
| WO | WO-2007/097754 | 8/2007 |
| WO | WO-2010/022387 | 2/2010 |
| WO | WO-2010/077329 | 7/2010 |
| WO | WO-2015/153482 | 10/2015 |

(56)                    References Cited

FOREIGN PATENT DOCUMENTS

WO       WO-2015153482 A1 * 10/2015    ............. A61B 5/145
WO       WO-2017/011346          1/2017

OTHER PUBLICATIONS

U.S. Appl. No. 15/926,919 (U.S. Pat. No. 11,596,330), Mar. 20, 2018 (Mar. 7, 2023).
U.S. Appl. No. 15/926,919, filed Feb. 1, 2023 Issue Fee Payment.
U.S. Appl. No. 15/926,919, filed Nov. 1, 2022 Notice of Allowance.
U.S. Appl. No. 15/926,919, filed Aug. 19, 2022 Response to Non-Final Office Action.
U.S. Appl. No. 15/926,919, filed May 20, 2022 Non-Final Office Action.
U.S. Appl. No. 15/926,919, filed Jan. 20, 2022 Response to Non-Final Office Action.
U.S. Appl. No. 15/926,919, filed Oct. 20, 2021 Non-Final Office Action.
U.S. Appl. No. 15/926,919, filed Oct. 20, 2021 After Final Consideration Program Decision.
U.S. Appl. No. 15/926,919, filed Aug. 16, 2021 After Final Consideration Program Request.
U.S. Appl. No. 15/926,919, filed Aug. 16, 2021 Response to Final Office Action.
U.S. Appl. No. 15/926,919, filed Jun. 15, 2021 Final Office Action.
U.S. Appl. No. 15/926,919, filed Feb. 16, 2021 Response to Non-Final Office Action.
U.S. Appl. No. 15/926,919, filed Nov. 16, 2020 Non-Final Office Action.
U.S. Appl. No. 15/926,919, filed Jul. 31, 2020 Response to Restriction Requirement.
U.S. Appl. No. 15/926,919, filed Jul. 1, 2020 Restriction Requirement.
Armour, J. C., et al., "Application of Chronic Intravascular Blood Glucose Sensor in Dogs", Diabetes, vol. 39, 1990, pp. 1519-1526.
Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454-462.
Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.
Bennion, N., et al., "Alternate Site Glucose Testing: A Crossover Design", Diabetes Technology & Therapeutics, vol. 4, No. 1, 2002, pp. 25-33.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
Boyne, M. S., et al., "Timing of Changes in Interstitial and Venous Blood Glucose Measured With a Continuous Subcutaneous Glucose Sensor", Diabetes, vol. 52, Nov. 2003, pp. 2790-2794.
Bremer, T. M., et al., "Benchmark Data from the Literature for Evaluation of New Glucose Sensing Technologies", Diabetes Technology & Therapeutics, vol. 3, No. 3, 2001, pp. 409-418.
Brooks, S. L., et al., "Development of an On-Line Glucose Sensor for Fermentation Monitoring", Biosensors, vol. 3, 1987/88, pp. 45-56.
Cass, A. E., et al., "Ferrocene-Medicated Enzyme Electrode for Amperometric Determination of Glucose", Analytical Chemistry, vol. 56, No. 4, 1984, 667-671.
Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Eren-Oruklu, M., et al., "Estimation of Future Glucose Concentrations with Subject-Specific Recursive Linear Models", Diabetes Technology & Therapeutics vol. 11(4), 2009, pp. 243-253.
Extended European Search Report dated Sep. 23, 2020 in Application No. EP 18772038.
Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004, pp. 1.
Garg, S., et al., "Improvement in Glycemic Excursions with a Transcutaneous, Real-Time Continuous Glucose Sensor", Diabetes Care, vol. 29, No. 1, 2006, pp. 44-50.
Hovorka, R., et al., "Nonlinear Model Predictive Control of Glucose Concentration in Subjects with Type 1 Diabetes", Physiological Measurement, vol. 55, Jul. 2004, pp. 905-920.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Kovatchev, B. P., et al., "Graphical and Numerical Evaluation of Continuous Glucose Sensing Time Lag", Diabetes Technology & Therapeutics, vol. 11, No. 3, 2009, pp. 139-143.
Kuure-Kinsey, M., et al., "A Dual-Rate Kalman Filter for Continuous Glucose Monitoring", Proceedings of the 28th IEEE, EMBS Annual International Conference, New York City, 2006, pp. 63-66.
Li, Y., et al., "In Vivo Release From a Drug Delivery MEMS Device", Journal of Controlled Release, vol. 100, 2004, pp. 211-219.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain the Newest Short-Range Connectivity Technology", Smart Computing Learning Series, Wireless Computing, vol. 8, Issue 5, 2002, pp. 72-74.
Malin, S. F., et al., "Noninvasive Prediction of Glucose by Near-Infrared Diffuse Reflectance Spectroscopy", Clinical Chemistry, vol. 45, No. 9, 1999, pp. 1651-1658.
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, vol. 3, No. 3, 2001, pp. 367-376.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedings of the 2005 IEEE, 2005, pp. 298-301.

(56)         References Cited

OTHER PUBLICATIONS

Panteleon, A. E., et al., "The Role of the Independent Variable to Glucose Sensor Calibration", Diabetes Technology & Therapeutics, vol. 5, No. 3, 2003, pp. 401-410.

Parker, R., et al., "Robust H∞ Glucose Control in Diabetes Using a Physiological Model", AIChE Journal, vol. 46, No. 12, 2000, pp. 2537-2549.

PCT Application No. PCT/US2018/023426, International Search Report and Written Opinion of the International Searching Authority mailed May 24, 2018.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Steil, G. M., et al., "Closed-Loop Insulin Delivery—the Path of Physiological Glucose Control", Advanced Drug Delivery Reviews, vol. 56, 2004, pp. 125-144.

Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27-31.

Sternberg, R., et al., "Study and Development of Multilayer Needle-Type Enzyme-Based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G., et al., "Strategies for Calibrating a Subcutaneous Glucose Sensor", Biomedica Biochimica Acta, vol. 48, 1989, pp. 957-964.

Wilson, G. S., et al., "Progress Toward the Development of an Implantable Sensor for Glucose", Clinical Chemistry, vol. 38, No. 9, 1992, pp. 1613-1617.

Cameron, F. et al., "Probabilistic Evolving Meal Detection and Estimation of Meal Total Glucose Appearance," Journal of Diabetes Science and Technology, vol. 3, Issue 5, Sep. 2009; pp. 1022-1030.

Extended European Search Report in counterpart European Application No. 25186924.4 mailed Nov. 6, 2025; 14 pages.

* cited by examiner

100

Fasting Glucose Analysis
Median: 102 mg/dL
Min: 95 mg/dL
Max: 109 mg/dL
Diagnosis: Pre diabetes

Post Prandial Glucose Analysis
Median: 150 mg/dL
Max: 203 mg/dL
Diagnosis: Impaired glucose tolerance

METHODS, DEVICES AND SYSTEM FOR PROVIDING DIABETIC CONDITION DIAGNOSIS AND THERAPY

RELATED APPLICATIONS

The present application is a continuation of U.S. patent application Ser. No. 15/926,919, filed Mar. 20, 2018, which claims priority to U.S. Provisional Application No. 62/474,605, filed Mar. 21, 2017, entitled "Methods, Devices and System for Providing Diabetic Condition Diagnosis and Therapy," the disclosures of each of which are incorporated herein by reference for all purposes.

BACKGROUND

The detection and/or monitoring of glucose levels or other analytes, such as lactate, oxygen, A1C, or the like, in certain individuals is vitally important to their health. For example, monitoring of glucose level is particularly important to individuals with diabetes and those with conditions indicative of onset of diabetes, in particular to identify physiological conditions that precede the onset of diabetes. If such physiological conditions can be identified in a timely manner, treatment or therapy by way of medication, exercise regimen, and/or modification to diet can effectively diminish the likelihood of diabetic conditions.

Techniques exist to determine if an individual has diabetes or has conditions indicative of onset of diabetic conditions, but these have drawbacks. Such techniques include fasting glucose test and oral glucose tolerance test. A fasting glucose test requires the individual to refrain from eating (i.e., fast) for a certain number of hours (e.g., 8 hours) before performing a blood glucose measurement. Consistent blood glucose measurement below 100 mg/dL is considered normal, measurements that are between 100 mg/dL and 126 mg/dL are considered to represent pre-diabetic condition, and measurements that are greater than 126 mg/L are considered to indicate diabetic condition. These are guidelines to assist physicians in their assessments of individuals suspected of having onset of diabetes. However, fasting for a prolonged period of time before the blood glucose measurement is performed may be inconvenient or not possible with certain individuals, resulting in potentially undiagnosed pre-diabetic or diabetic conditions.

An oral glucose tolerance test also requires that the individual refrain from eating for a predetermined time period (e.g., 8 hours) before performing a blood glucose measurement. Immediately following the blood glucose measurement after fasting for the predetermined time period, as part of the oral glucose tolerance test, the individual drinks a 75 gram oral dose of glucose solution. Two hours after drinking the glucose solution, a second blood glucose measurement is performed. A second blood glucose measurement of below 140 mg/dL is considered normal, a second blood glucose measurement between 140 mg/L and 200 mg/dL is considered to represent impaired glucose tolerance condition, and a second blood glucose measurement that is greater than 200 mg/dL is considered to indicate diabetic condition. In addition to the lengthy process for performing the oral glucose tolerance test, many find the need to drink the glucose solution as part of the test to be distasteful and undesirable. In some contexts, these drawbacks are significant enough to cause an individual to forego performing the oral glucose tolerance test, potentially resulting in undiagnosed pre-diabetic or diabetic conditions. Accordingly, there is an ongoing desire and an important need to improve glycemic control of individuals and in particular, to accurately and timely diagnose the onset of diabetes as well as diabetic condition itself in a way that is convenient, accurate, and timely.

SUMMARY

Embodiments of the present disclosure include methods, devices and systems for determining fasting glucose level information, that include performing meal start time determination for each one day time period, determining a plurality of fasting metrics, each fasting metric corresponding to a respective one day time period, determining an overall fasting metric, and generating fasting glucose level information.

Certain embodiments for the meal start time determination include retrieving from a storage unit a meal start time of day period, retrieving an insulin delivery data within the meal start time of day period, determining a potential meal start time within the meal start time of day period, comparing the insulin delivery information with the potential meal start time, and setting the meal start time as the determined potential meal start time when the insulin delivery information correlates with the potential meal start time based on the comparison.

Certain embodiments for determining fasting glucose level information includes an apparatus with one or more processors, and a storage unit operatively coupled to the one or more processors and configured to store instructions which, when executed by the one or more processors, controls the one or more processors to perform meal start time determination for each one day time period, to determine a plurality of fasting metrics, each fasting metric corresponding to a respective one day time period, to determine an overall fasting metric, and to generate fasting glucose level information.

A system for determining fasting glucose level information, in certain embodiments, includes an in vivo glucose sensor operatively coupled to the one or more processors, the glucose sensor having a portion positioned under a skin surface and in contact with bodily fluid and configured to generate signals corresponding to monitored glucose level in the bodily fluid, a glucose monitor operatively coupled to the glucose sensor to process the signals from the glucose sensor and to generate glucose measurement data, a data processing device in signal communication with the glucose monitor to receive the glucose measurement data, the data processing device including: one or more processors, and a storage unit operatively coupled to the one or more processors and configured to store instructions which, when executed by the one or more processors, controls the one or more processors to perform meal start time determination for each one day time period, to determine a plurality of fasting metrics, each fasting metric corresponding to a respective one day time period, to determine an overall fasting metric, and to generate fasting glucose level information.

The system for determining fasting glucose level information in certain embodiments includes an insulin delivery device in signal communication with the data processing device, where the insulin delivery device is configured to provide insulin delivery information to the data processing device, and further, where the data processing device is configured to retrieve from the storage unit a meal start time of day period, to identify an insulin delivery information within the meal start time of day period received from the insulin delivery device, to determine a potential meal start time within the meal start time of day period, to compare the insulin delivery information with the potential meal start time, and to set the meal start time as the determined potential meal start time when the insulin delivery information correlates with the potential meal start time based on the comparison. For example, insulin delivery devices (e.g., devices integrating an infusion device therein) to administer insulin therapy to patients may administer and modify basal profiles, as well as determine appropriate boluses for administration based on, among others, the detected analyte levels.

Embodiments of the present disclosure further include methods, devices and systems for performing post-prandial glucose level analysis that include performing meal start time determination for each one day time period, determining a post-prandial metric for each day based on the meal start time for the corresponding day, determining an overall post-prandial metric from the plurality of the post-prandial metric for each day, and generating a post-prandial glucose level information.

Certain embodiments for determining the post-prandial metric for each day includes retrieving glucose data for a first time period relative to the meal start time, determining a pre-meal glucose parameter from the retrieved glucose data for the first time period, retrieving glucose data for a second time period relative to the meal start time, determining a post-meal glucose parameter from the retrieved glucose data for the second time period, and determining a post-prandial glucose metric from the pre-meal and post-meal glucose parameters.

An apparatus for performing post-prandial glucose level information analysis, in certain embodiments, includes one or more processors, and a storage unit operatively coupled to the one or more processors and configured to store instructions which, when executed by the one or more processors, controls the one or more processors to perform meal start time determination for each one day time period, to determine a post-prandial metric for each day based on the meal start time for the corresponding day, to determine an overall post-prandial metric from the plurality of the post-prandial metric for each day, and to generate a post-prandial glucose level information.

A system for performing post-prandial glucose level information analysis, in certain embodiments, includes an in vivo glucose sensor operatively coupled to the one or more processors, the glucose sensor having a portion positioned under a skin surface and in contact with bodily fluid and configured to generate signals corresponding to monitored glucose level in the bodily fluid, a glucose monitor operatively coupled to the glucose sensor to process the signals from the glucose sensor and to generate glucose measurement data, a data processing device in signal communication with the glucose monitor to receive the glucose measurement data, the data processing device including: one or more processors, and a storage unit operatively coupled to the one or more processors and configured to store instructions which, when executed by the one or more processors, controls the one or more processors to perform meal start time determination for each one day time period, to determine a post-prandial metric for each day based on the meal start time for the corresponding day, to determine an overall post-prandial metric from the plurality of the post-prandial metric for each day, and to generate a post-prandial glucose level information.

In this manner, accurate and reliable fasting glucose determination and post-prandial glucose tolerance determination are provided to the individuals for pre-diabetes or diabetic condition diagnosis without the need for the individuals to perform inconvenient and cumbersome fasting glucose test, nor to require consumption of distasteful glucose solution as part of an oral glucose tolerance test.

These and other features, objects and advantages of the present disclosure will become apparent to those persons skilled in the art upon reading the details of the present disclosure as more fully described below.

DETAILED DESCRIPTION

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Figure 1A:
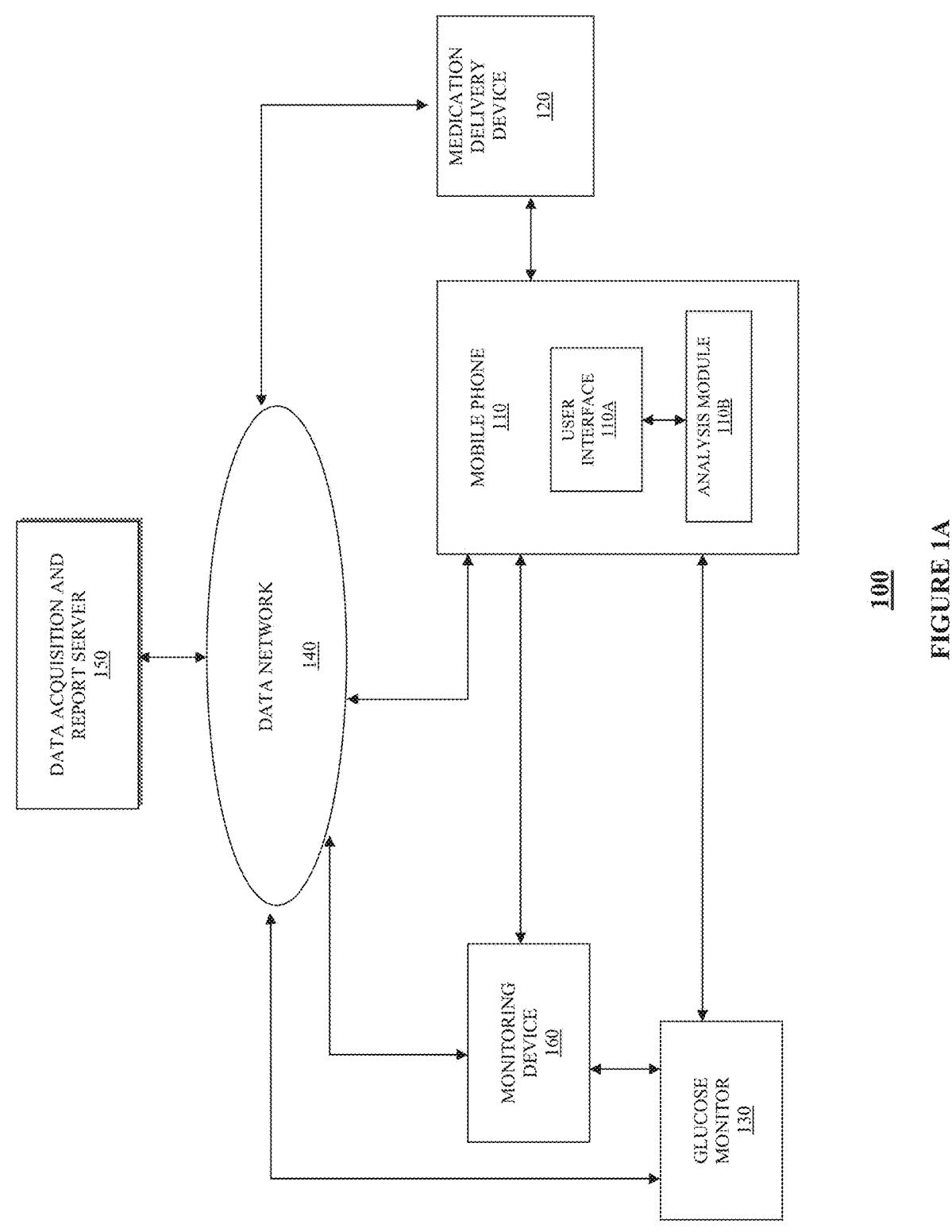
FIG. 1A is a system for providing fasting glucose analysis and post-prandial glucose tolerance analysis in accordance with one embodiment of the present disclosure.

FIG. 1A is a system for providing fasting glucose analysis and post-prandial glucose tolerance analysis in accordance with one embodiment of the present disclosure. Referring to the FIG. 1A, diagnosis and therapy system 100, in certain embodiments, includes a data network 140 operatively coupled to data acquisition and report server 150. As shown, diagnosis and therapy system 100 also includes mobile phone 110 including user interface 110A and analysis module 110B programmed in the mobile phone 110 as a software application ("App") that is executable by any processor controlled device, and in particular, a smart phone with communication capabilities to receive, analyze, transfer, transmit, display or output or nonactionable, actionable information, for example, including medical condition diagnosis based on the received glucose data analysis. In certain embodiments, the App is installed in the mobile phone 110 as a downloaded executable file over data network 140 from server 150. As discussed in further detail below, in certain embodiments, the App is configured to provide or output on the user interface 110A diagnosis information such as pre-diabetes condition, and/or impaired glucose tolerance condition from the real time glucose level information.

Referring to FIG. 1A, also included in diagnosis and therapy system 100 is glucose monitor 130 and monitoring device 160 each operatively coupled to and in bi-directional communication with data network 140 and mobile phone 110. Also shown in FIG. 1A is medication delivery device 120 also operatively coupled to and in bi-directional communication with data network 140 and mobile phone 110. The communication between mobile phone 110, medication delivery device 120, glucose monitor 130, monitoring device 160 and data network 140 includes one or more wireless communication, wired communication, Bluetooth® communication, WiFi data communication, radio frequency identification (RFID) enabled communication, Zigbee® communication, or any other suitable data communication that optionally supports data encryption/decryption, data compression, data decompression and the like.

Glucose monitor 130 shown in FIG. 1A includes one or more in vivo glucose sensors, each with a portion configured to be in fluid contact with bodily fluid of a user under a skin surface, and coupled to sensor electronics attached or mounted on the skin surface for processing signals from the glucose sensor and communicating the processed glucose signals to one or more of mobile phone 110, monitoring device 160, data acquisition and report server 150, and medication delivery device 120 over a direct communication link with the one or more of these devices, or alternatively, over the data network 140. Further, monitoring device 160 includes, in certain embodiments, compact, handheld data processing devices that are configured for communication with the glucose monitor 130 and for further processing data received from the glucose monitor 130, and optionally to program, diagnose, or otherwise monitor the operation of glucose monitor 130. Additional details on the glucose monitor 130 including glucose sensor and sensor electronics and monitoring device 160 can be found in U.S. Pat. No. 6,175,752 and US Patent Publication No. 2011/0213225, both assigned to the assignee of the present application, Abbott Diabetes Care Inc., Alameda, California, the disclosures of each of which are incorporated herein by reference for all purposes.

Figure 1B:
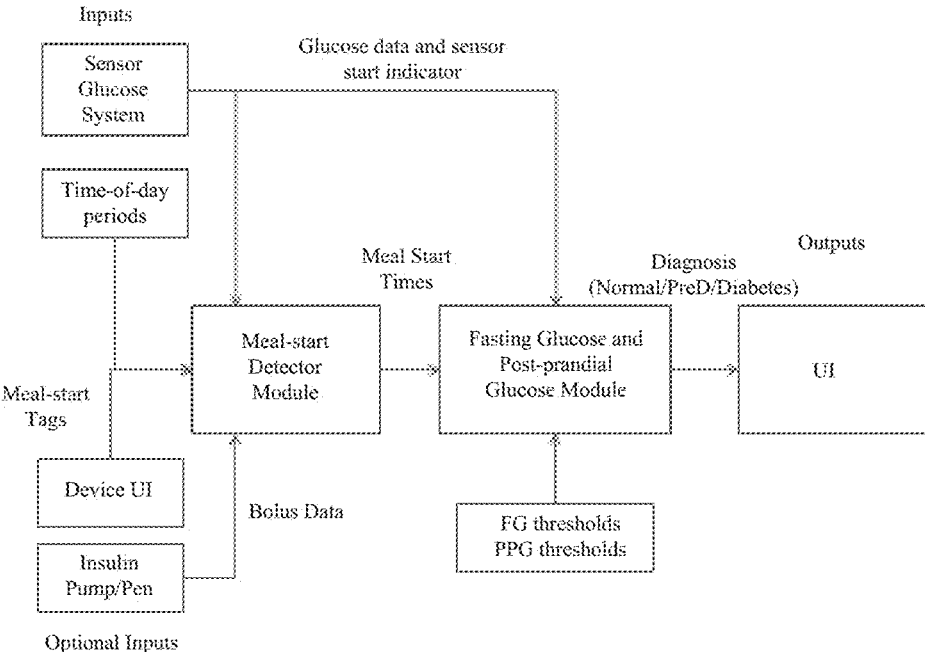
FIG. 1B is a data flow for providing fasting glucose analysis and post-prandial glucose tolerance analysis of the overall system of FIG. 1A in accordance with one embodiment of the present disclosure.

FIG. 1B is a data flow for providing fasting glucose analysis and post-prandial glucose tolerance analysis of the overall system of FIG. 1A in accordance with one embodiment of the present disclosure. Referring to FIG. 1B, in certain embodiments, one or more of monitored glucose level information, time of day period information, meal start tag/time stamp information, insulin delivery time information and/or other user initiated information is provided to the analysis module 110B and/or to the data acquisition and report server 150 to perform fasting glucose analysis and/or post-prandial glucose tolerance analysis. As shown in FIG. 1B, in certain embodiments, the analysis module 110B and/or the data acquisition and report server 150 includes a meal start detector module, a fasting glucose and post-prandial glucose module as well as one or more storage units such as non-volatile memory devices to store received data and one or more threshold parameters associated with the fasting glucose analysis and/or the-post prandial glucose analysis. Referring again to FIG. 1B, the result(s) of the fasting glucose analysis and/or post-prandial glucose tolerance analysis is presented on the user interface 110A of the mobile telephone 110, a user interface of the monitoring device 160 (FIG. 1) and/or a computer terminal 170 (FIG. 1C) as discussed in conjunction with FIG. 1C below.

Figure 1C:
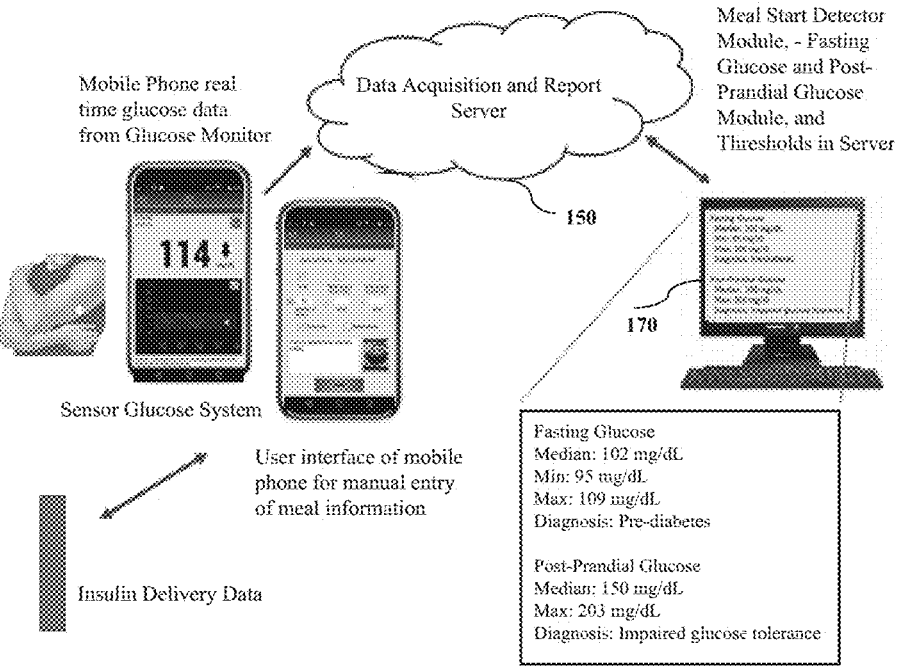
FIG. 1C is an overall system for providing fasting glucose analysis and post-prandial glucose tolerance analysis in accordance with another embodiment of the present disclosure.

FIG. 1C is a system for providing fasting glucose analysis and post-prandial glucose tolerance analysis in accordance with embodiments of the present disclosure. In certain embodiments, some or all of the functions of the App related to the fasting glucose analysis and/or the post-prandial glucose analysis are implemented by data acquisition and report server 150 to provide diagnosis information such as pre-diabetes condition, and/or impaired glucose tolerance condition from the real time glucose level information. As shown in FIG. 1C, information from glucose monitor 130 and/or monitoring device 160 and/or medication delivery device 120 are pushed automatically and/or periodically to data acquisition and report server 150 for analysis. In certain embodiments, information/data from one or more of glucose monitor 130, monitoring device 160 and medication delivery device 120 is communicated to mobile phone 110. Upon receipt of the information/data, mobile phone 110 is configured to communicate the received information/data to data acquisition and report server 150 for analysis. In this manner, in an embodiment, mobile phone 110 is configured to operate as a data conduit or transfer device to collect information/data and transfer the received information/data to data acquisition and report server 150 for analysis.

Further, in certain embodiments, one or more of the glucose monitor 130, monitoring device 160 and medication delivery device 120 are each configured with the App for execution therein locally. In other words, embodiments of the present disclosure include one or more of the glucose monitor 130, monitoring device 160, medication delivery device 120 that includes analysis module 110B for processing glucose data, medication delivery information, time of day period data, among others, and to generate diagnosis information such as pre-diabetes condition and/or impaired glucose tolerance condition based on the real time glucose level information.

Figures 2, 3:
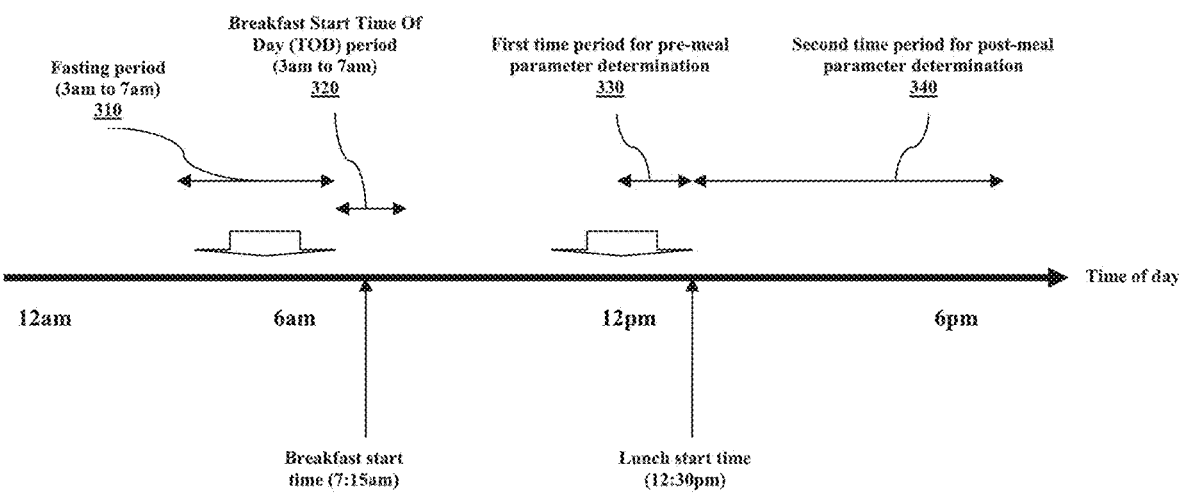
FIG. 2 is an exemplary output display of the fasting glucose analysis and post-prandial glucose tolerance analysis from the overall systems of FIGS. 1A and 1C in accordance with one embodiment of the present disclosure.
FIG. 3 is an exemplary time line for the fasting glucose analysis and the post-prandial glucose analysis in accordance with one embodiment of the present disclosure.

FIG. 2 is an example output display of the fasting glucose analysis and post-prandial glucose tolerance analysis in accordance with one embodiment of the present disclosure. Referring to FIG. 2, in certain embodiments, the App in analysis module 110B of the mobile phone 110 performs fasting glucose level analysis and post-prandial glucose level analysis (to determine glucose tolerance level), and outputs the diagnosis information on user interface 110A. In another embodiment, the data acquisition and report server 150 performs fasting glucose level analysis and post-prandial glucose level analysis (to determine glucose tolerance level), and pushes the results of the analysis to the display of the physician's computer terminal 170 (FIG. 1C) to provide diagnosis information. As shown, the results of the fasting glucose level analysis includes, for example, but not limited to, median glucose level (102 mg/L), minimum glucose level (95 mg/dL) and maximum glucose level (109 mg/dL), with a diagnosis indication showing "pre-diabetes" condition. Also shown in FIG. 2 is the post-prandial glucose level analysis including, for example, median glucose level (150 mg/dL), and maximum glucose level (203 mg/dL) with a corresponding diagnosis indication of "impaired glucose tolerance" condition.

Referring again to FIG. 2, while mobile phone 110 is provided with user interface 110A, each of the medication delivery device 120, monitoring device 160, and glucose monitor 130, in certain embodiments, includes a display or user interface that is configured to output the same information shown in FIG. 2 locally on the respective devices.

In embodiments, medication delivery device 120 may include an infusion device such as an insulin infusion pump or the like, which may be configured to administer insulin to patients. In alternatives, a device may be configured to integrate an infusion device therein so that the device is configured to administer insulin (or other appropriate drug) therapy to patients, for example, for administering and modifying basal profiles, as well as for determining appropriate boluses for administration based on the detected analyte levels received from a source, such as the sensors of the glucose monitor.

FIG. 3 is an exemplary time line for the fasting glucose analysis and the post-prandial glucose analysis in accordance with one embodiment of the present disclosure. As discussed in further detail in conjunction with FIGS. 4A-4B and 5A-5B, each of the fasting glucose level analysis and the post-prandial glucose level analysis uses glucose level information, for example from the in vivo glucose sensor of glucose monitor 130 (FIG. 1) positioned in fluid contact with bodily fluid under the skin surface, over a sensor wear (sensor life) time period—for the duration of the glucose sensor wear of 7 days, 10 days, 14 days, one month, two months, three months, six months or more. In certain embodiments, the glucose data from the glucose sensor are received or collected at a predetermined time interval such as every minute, every five minutes, every 10 minutes, every 15 minutes, or more, and stored in a memory or storage device of the glucose monitor 130 and thereafter communicated to the one or more monitoring device 160, mobile phone 110, medication delivery device 120 and the data acquisition and report server 150.

In embodiments, the bodily fluid may be dermal fluid or interstitial fluid.

Referring again to FIG. 3, and as discussed in further detail below, in certain embodiments, meal start time of day (TOD) period associated with a meal start time (e.g., breakfast start time of day (TOD) period 320 shown in FIG. 3) is stored in one or more storage devices of one or more of monitoring device 160, mobile phone 110, medication delivery device 120 and the data acquisition and report server 150. Also shown in FIG. 3 is fasting period 310 associated with breakfast start time. In certain embodiments, and as discussed in further detail below, the breakfast start TOD period 320, fasting period 310, and breakfast start time (7:15 am) are used with glucose level information obtained from an in vivo glucose sensor to perform fasting glucose analysis.

Referring still to FIG. 3 and as discussed in further detail below, in certain embodiments, meal start time is determined for each meal during a 24 hour period. Then, two time periods as shown in FIG. 3 (for example, in conjunction with lunch start time) such as a first time period for pre-meal parameter determination 330 and a second time period for post-meal parameter determination 340 are retrieved from the storage unit or memory device of mobile phone 110 or at data acquisition and report server 150, for example, and used in conjunction with the determined meal start time to perform post-prandial glucose analysis. Additional detailed description of the automatic or programmed meal start detection routine is described in PCT Patent Publication No. WO 2015/153482, assigned to the assignee of the present disclosure, and the disclosure of which is incorporated by reference in its entirety for all purposes.

Figure 4A:
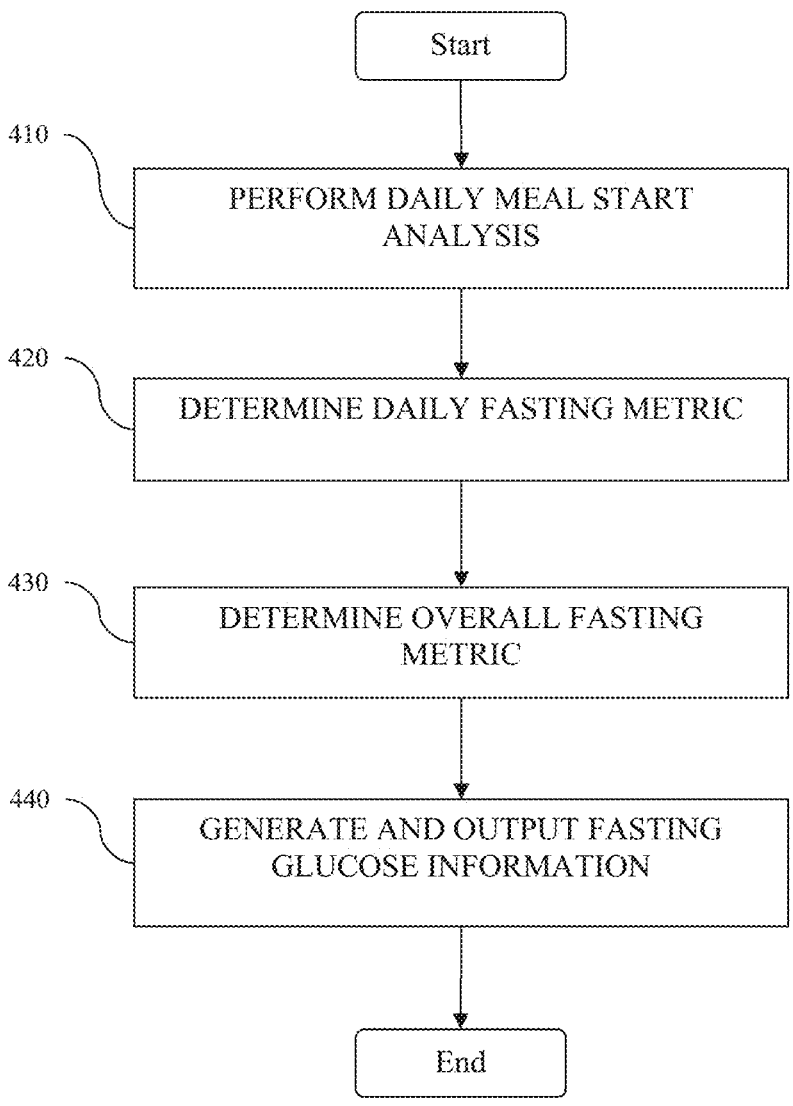
FIG. 4A is a flowchart illustrating a routine to determine fasting glucose level information in accordance with one embodiment of the present disclosure.

FIG. 4A is a flowchart illustrating a routine to determine fasting glucose level information in accordance with one embodiment of the present disclosure. Referring to FIG. 4A, fasting glucose level analysis in certain embodiments include performing daily meal start determination analysis (410) to determine the start time of the first meal of the day. Thereafter a fasting metric for each day with the start time of the first meal of the day is determined (420).

In certain embodiments, the daily fasting metric is determined, for example, by retrieving glucose data received from the glucose monitor 130 (FIG. 1) for a fasting period (FIG. 3) corresponding to the determined meal start time. In certain embodiments, the fasting period spans the time period from 4 hours and 15 minutes before the meal start time to 15 minutes before the meal start time. That is, in one embodiment, the fasting period is a 4 hour period before the meal start time that ends 15 minutes before the meal start time. While 4 hours and 15 minutes are used herein, these values for the fasting period are non-limiting examples only and are not intended to limit the scope of the present disclosure with these values. Rather, within the scope of the present disclosure, the fasting time period can including other time periods (for example, 3 hours, 3.5 hours, 4 hours, 4.5 hours, 5 hours, 5.5 hours, 6 hours, and/or any other suitable time ranges including intervening time ranges) that precede the determined meal start time. Further, the 15 minutes preceding the meal start time by which the fasting period ends is described herein solely as a non-limiting example, and other suitable time ranges can be used within the scope of the present disclosure (for example, 10 minutes, 15 minutes, 20 minutes, 25 minutes, or any other suitable time ranges including intervening times).

Referring back to FIG. 4A, after retrieving the glucose data for the fasting period (FIG. 3) corresponding to the determined meal start time, the daily fasting metric is determined, in certain embodiments, by calculating the median of the retrieved glucose data for the fasting period. In other embodiments, the daily fasting metric is determined by identifying the glucose level at a predetermined time preceding the meal start time (for example, at 15 minutes before the determined meal start time). Alternatively, daily fasting metric is determined by taking the mean, minimum, maximum, or other suitable metric of the glucose data over the fasting period.

With the determined daily fasting metric, an overall fasting metric from the plurality of daily fasting metric is determined for the time period spanning the number of days for which daily fasting metric is determined (430). Using the overall fasting metric, fasting glucose level information as shown in FIG. 2 is generated and output to the user interface (440). In certain embodiments, the determination of the overall fasting metric across all days that have a valid daily fasting metric includes determining one or more of a median, mean, standard deviation, inter-quartile range (IQR), a minimum, and a maximum of the fasting metric for all days with valid daily fasting metric.

Figure 4B:
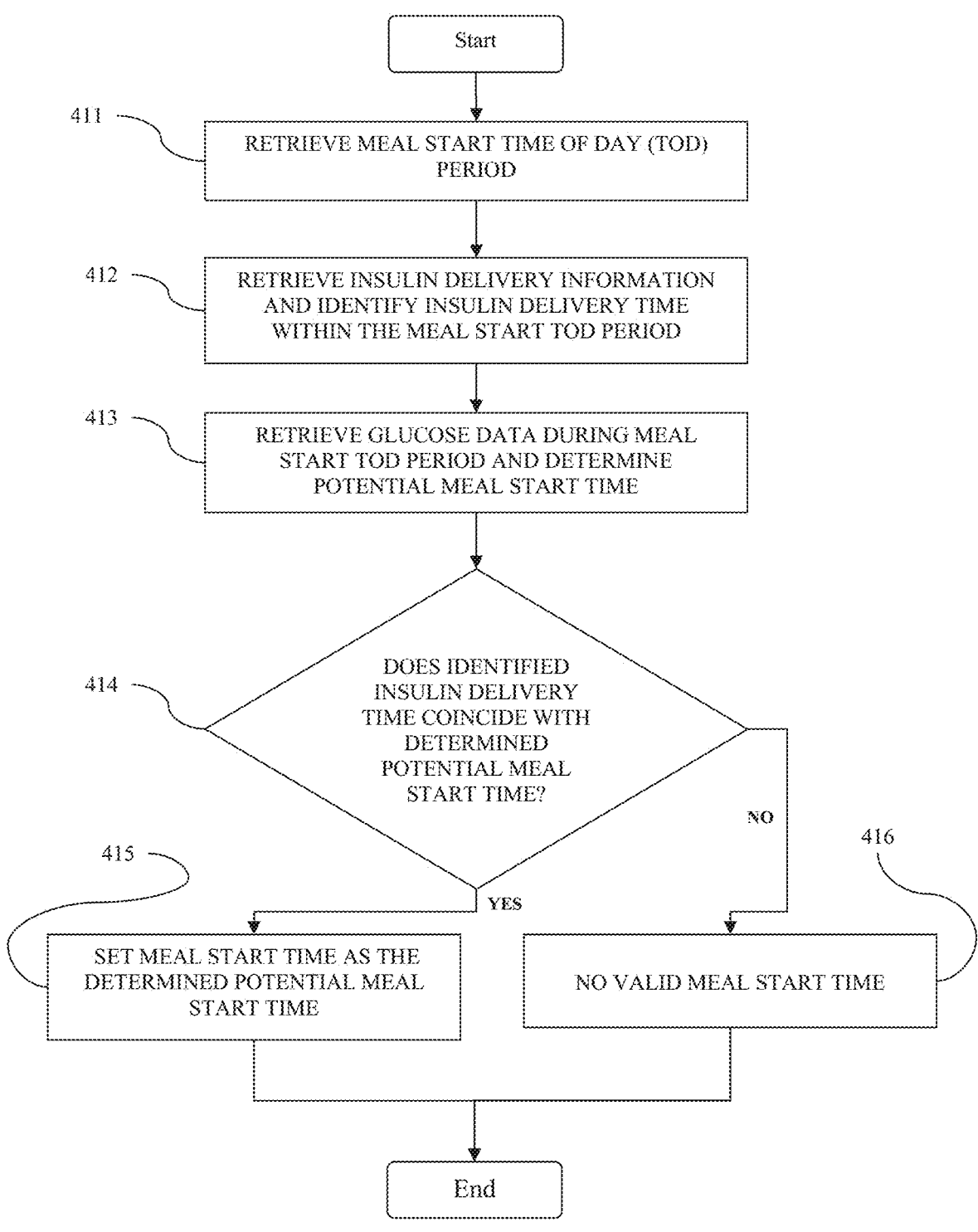
FIG. 4B is a flowchart illustrating a routine to perform daily meal start determination in the fasting glucose level information determination routine of FIG. 4B in accordance with one embodiment of the present disclosure.

FIG. 4B is a flowchart illustrating a routine to perform daily meal start determination in the fasting glucose level information determination routine of FIG. 4B in accordance with one embodiment of the present disclosure. Referring to FIG. 4B, in certain embodiments, meal start determination includes retrieving meal start TOD period from memory or from a previously stored setting (411). Thereafter, insulin delivery information is retrieved and insulin delivery time within the meal start TOD period is identified (412). Also, glucose data during the meal start TOD period is retrieved and a potential meal start time is determined by analyzing the retrieved glucose data during the meal start TOD period (413). In certain embodiments, the potential meal start time is determined from the retrieved glucose data by isolating or identifying the beginning of a sustained glucose level change in direction. In certain embodiments, potential meal start times are determined by identifying upward trend in glucose following a rapid acting insulin delivery marker (e.g., bolus delivery time), identifying an upward trend in the monitored glucose level following a meal marker, or identifying the insulin delivery marker or the meal marker as the start of the meal.

Referring back to FIG. 4B, the retrieved insulin delivery time is compared with the potential meal start time to determine whether the retrieved insulin delivery time correlates with the potential meal start time (414). If the retrieved insulin delivery time does not correlate with the potential meal start time, then no valid meal start time is identified (416) that corresponds with the meal start TOD period. On the other hand, if the retrieved insulin delivery time correlates or coincides with the potential meal start time, then the meal start time is set to the determined potential meal start time (415).

In certain embodiments, when there is no insulin delivery information available, meal start tag (user initiated) can be used in the analysis by, for example, comparing the time information associated with the meal start tag to determine whether the potential meal start time correlates with the meal start tag. If the potential meal start time correlates with the meal start tag, the potential meal start time is identified as the meal start time for the retrieved meal start TOD period. In certain embodiments, the meal start time is determined based on a user initiated meal event tag using the user interface 110A of mobile phone 110, for example, when the user manually indicates the start of the meal event. In still other embodiments, the time information associated with the meal start tag can be used as the meal start time. Within the scope of the present disclosure, insulin delivery time or time information for the meal start tag can be used, depending on which is available for the meal start TOD period, to confirm the meal start time.

In this manner, referring back to FIGS. 4A-4B, fasting glucose level information is determined by analyzing the stored glucose measurement data and provided to the user or the physician. With the fasting glucose level information, the App may provide diagnosis information, such as, for example, "pre-diabetes" condition (FIG. 2). With the diagnosis information, the user is able to make informed and timely corrective action, under the guidance of a physician, for example, to take medication, modify diet, implement exercise regimen, and the like.

In certain embodiment, the App may be configured to discard the identified and stored glucose measurement from the analysis data set that corresponds to the first 24 hour time period of the glucose sensor wear. This feature is configured to improve the accuracy of the fasting glucose level analysis by excluding glucose data that may suffer from aberrant signal such as can be observed upon sensor initiation periods, for example signal attenuation error. Additional detailed information on signal attenuation is provided in U.S. Pat. No. 8,583,205, assigned to the assignee of the present disclosure, the disclosure of which is incorporated by reference in its entirety for all purposes.

Figure 5A:
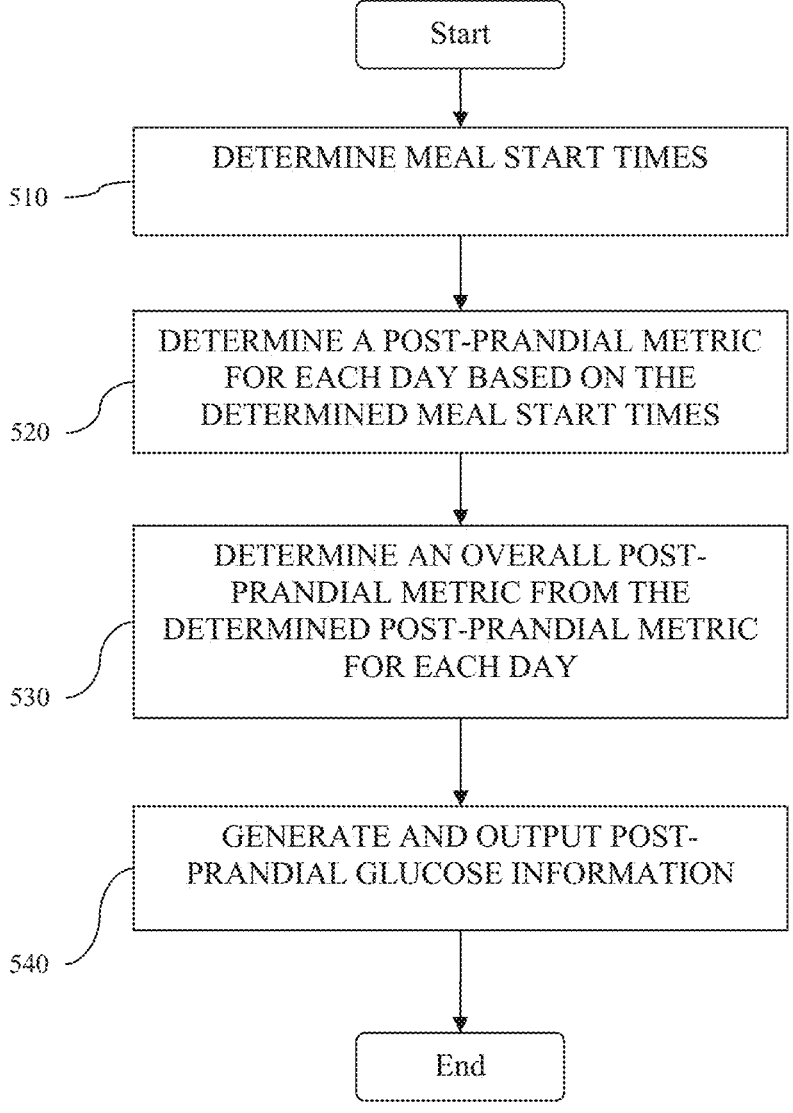
FIG. 5A is a flowchart illustrating a routine to determine post-prandial glucose level information in accordance with one embodiment of the present disclosure.

FIG. 5A is a flowchart illustrating a routine to determine post-prandial glucose level information in accordance with one embodiment of the present disclosure. Referring to FIG. 5A, for each day in the post-prandial glucose level information analysis time period, a corresponding meal start time is determined (510). In certain embodiments, the meal start time is determined as described above in conjunction with FIGS. 4A and 4B and thus, not repeated here. In this manner, for each day in the analysis time period, the meal start time for breakfast, lunch and dinner are determined. Thereafter, a post-prandial metric for each day is determined based on the meal start times (520). As discussed in further detail in conjunction with FIG. 5B below, the post-prandial metric for each day is determined using select glucose level information associated with the meal start times.

Referring to FIG. 5A, after determining the post-prandial metric for each day of the analysis time period, an overall post-prandial metric is determined using the post-prandial metric for each day (530), and the post-prandial glucose information from the overall post-prandial metric is generated and/or output to the user or the physician (540). For example, referring to FIG. 2, post-prandial glucose analysis includes a visual output of the median glucose level (e.g., 150 mg/dL) and maximum glucose level (e.g., 203 mg/dL), and a resulting diagnosis of "impaired glucose tolerance".

Figure 5B:
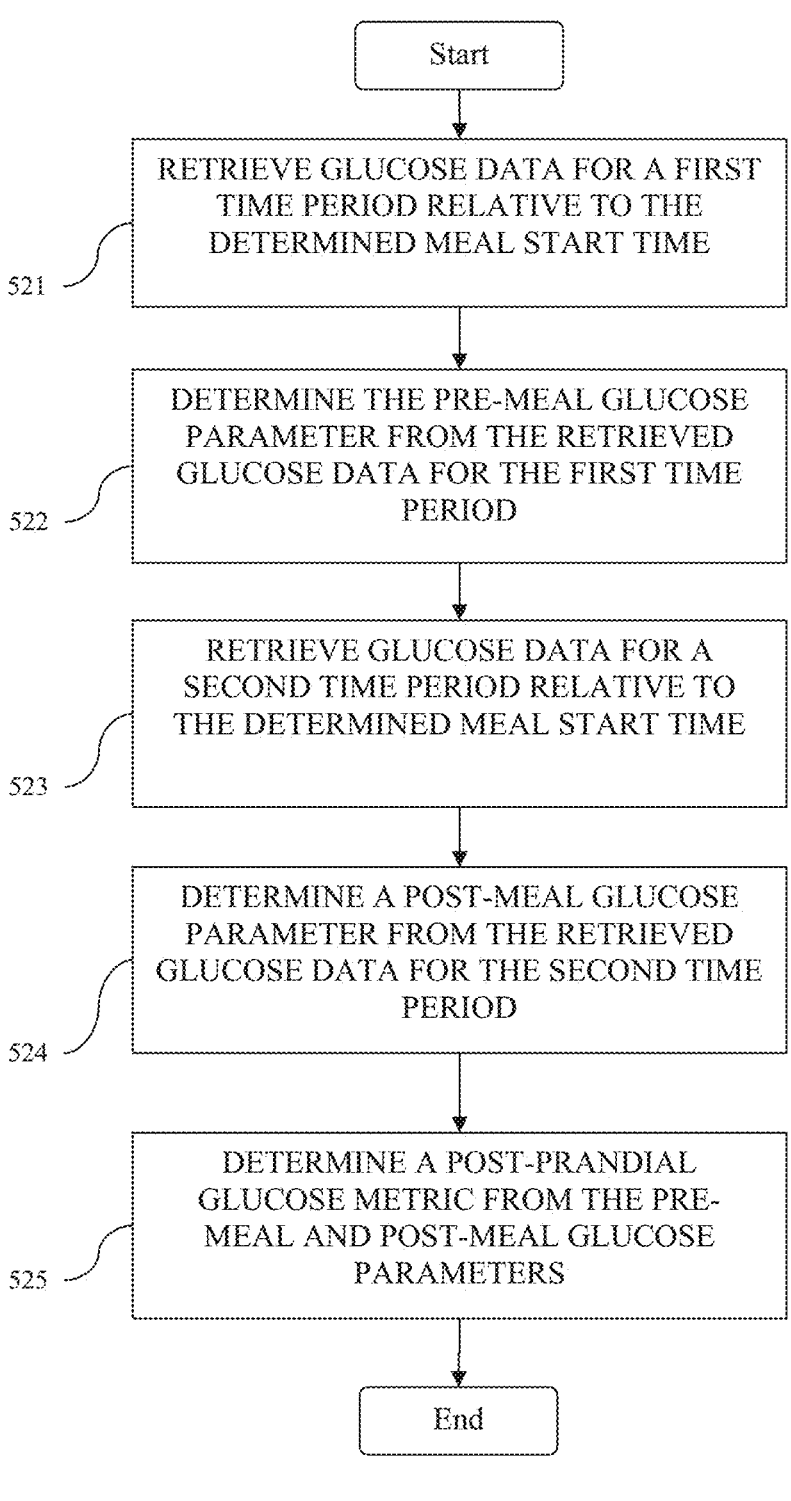
FIG. 5B is a flowchart illustrating a routine to determine a post-prandial metric for each day based on the determined meal start times in the post-prandial glucose level information determination routine of FIG. 5A in accordance with one embodiment of the present disclosure.

FIG. 5B is a flowchart illustrating a routine to determine a post-prandial metric for each day based on the meal start times in the post-prandial glucose level information determination routine of FIG. 5A in accordance with one embodiment of the present disclosure. Referring to FIG. 5B, for each determined meal start time, glucose data for a first time period relative to the meal start time is retrieved (521). For example, glucose data for 30 minutes (or other suitable time periods) before the meal start time is retrieved. While 30 minutes is used herein, within the scope of the present disclosure, other time periods can be used including, but not limited to, 20 minutes, 25 minutes, 30 minutes, 35 minutes, 40 minutes, 45 minutes, one hour or greater, or any other intervening time periods.

Thereafter, a pre-meal glucose parameter is determined from the glucose data for the first time period (522). In one embodiment, the pre-meal glucose parameter includes the median of the glucose data for the first time period. In other embodiments, the pre-meal glucose parameter includes a single glucose level identified within the first time period, or a median of the glucose data in the first time period. Referring back to FIG. 5B, glucose data for a second time period relative to the meal start time is retrieved (523). For example, glucose data for a 6 hour time period from the meal start time is retrieved for analysis. While 6 hour time period is selected here, within the scope of the present disclosure, other time periods can be used including, but not limited to, 4 hour, 5 hour, 6 hour, 7 hour or more, or any intervening time period. In another embodiment, the second time period starts with the meal start time and ends immediately prior to the next, subsequent meal start time. For example, the glucose data in the second time period includes all glucose data collected from the meal start time through the last glucose data point available before the next meal start time.

Referring again to FIG. 5B, a post-meal glucose parameter from the retrieved glucose data for the second time period is determined (524). In one embodiment, the post-meal glucose parameter includes a post-meal peak parameter determined by calculating the maximum glucose level from the glucose data in the second time period. In other embodiments, the post-meal glucose parameter includes a mean or median of the glucose data from the second time period. The post-prandial glucose metric is determined from the pre-meal glucose parameter and the post-meal glucose parameters (525). For example, in one embodiment, the post-prandial glucose metric includes a peak-difference metric, which is the difference between the post meal peak parameter (the maximum glucose level from the glucose data in the second time period) and the pre-meal glucose parameter (the median of the glucose data for the first time period).

In this manner, post-prandial glucose level analysis is performed in accordance with various embodiments of the present disclosure using glucose data received from glucose monitor 130 (FIG. 1). Referring again to FIG. 2, the diagnosis information output from the post prandial glucose level analysis is presented, e.g., visually, audibly, and the like, where the median glucose level (150 mg/dL) and maximum glucose level (203 mg/dL) are output with a diagnosis of "impaired glucose tolerance", or other notification. Similar to the diagnosis based on the fasting glucose level analysis described above, the diagnosis from the post prandial glucose level analysis described here provides physiological information from which the user can take corrective action, optionally under the guidance of a physician, to improve glycemic control by, for example, modifying diet, implementing an exercise regimen, and/or with medication. Output information, such as the diagnosis information, may be used for therapy-, administration- or treatment-related decisions.

Since the analysis relies on glucose measurement data from the glucose monitor 130 (FIG. 1) to provide diagnosis for identifying pre-diabetic condition or diabetic condition, the inconvenience of actual fasting as required for the conventional fasting glucose test, or the distasteful and undesirable experience of drinking glucose solution, and performing multiple blood glucose measurements as required for the conventional glucose tolerance test, are obviated by the embodiments of the present disclosure.

An apparatus for determining fasting glucose level information may comprise one or more processors; and a storage unit operatively coupled to the one or more processors and configured to store instructions which, when executed by the one or more processors, controls the one or more processors to perform meal start time determination for each one day time period, to determine a plurality of fasting metrics, each fasting metric corresponding to a respective one day time period, to determine an overall fasting metric, and to generate fasting glucose level information.

In an embodiment, the one or more processors executing the stored instructions to perform the meal start time determination is configured to retrieve from the storage unit a meal start time of day period, to retrieve an insulin delivery information within the meal start time of day period, to determine a potential meal start time within the meal start time of day period, to compare the insulin delivery information with the potential meal start time, and to set the meal start time as the determined potential meal start time when the insulin delivery information correlates with the potential meal start time based on the comparison. The retrieved insulin delivery information may include insulin delivery start time. The meal start time may be set as the potential meal start time when the insulin delivery information coincides with the potential meal start time. The retrieved insulin delivery information may include insulin delivery start time.

In another embodiment, the one or more processors executing the stored instructions to determine the potential meal start time is configured to retrieve glucose data collected during the meal start time of day period, and to determine the potential meal start time based on the retrieved glucose data.

In embodiments, the one or more processors executing the stored instructions to determine each fasting metric is configured to retrieve a plurality of glucose data collected over a fasting period, the fasting period preceding the meal start time, and to determine a median of the retrieved plurality of glucose data over the fasting period. The fasting period may span a predetermined time period that begins and ends before the meal start time. The end of the predetermined time period for the fasting period may precede the beginning of the meal start time by a predetermined amount of time. The one or more processors may be configured to apply a function to the determined fasting metric to determine the overall fasting metric. The function may include one or more of a median, a mean, a standard deviation, an interquartile range, a minimum, or a maximum.

In an aspect, the apparatus may further comprise a user interface is operatively coupled to the one or more processors, wherein the one or more processors is configured to generate and output diagnosis information based on the fasting glucose level information. The generated diagnosis information may provide an indication of diabetic condition. The diagnosis information may include a pre-diabetes condition.

In another aspect, the one or more processors may be configured to detect a meal start tag based on a user input to perform the meal start time determination for each one day time period.

In aspects, the apparatus may further include an in vivo glucose sensor operatively coupled to the one or more processors, the glucose sensor having a portion positioned under a skin surface and in contact with bodily fluid and configured to generate signals corresponding to monitored glucose level in the bodily fluid and that are stored in the storage unit as glucose measurement data. The bodily fluid may include dermal fluid, or interstitial fluid. The glucose sensor may include a plurality of electrodes including a working electrode comprising an analyte-responsive enzyme bonded to a polymer disposed on the working electrode. The analyte-responsive enzyme may be chemically bonded to the polymer disposed on the working electrode. The working electrode may comprise a mediator bonded to the polymer disposed on the working electrode. The mediator may be crosslinked with the polymer disposed on the working electrode.

In another aspect, the glucose sensor may include a plurality of electrodes including a working electrode comprising a mediator bonded to a polymer disposed on the working electrode.

A system for determining fasting glucose level information comprises an in vivo glucose sensor having a portion positioned under a skin surface and in contact with bodily fluid and configured to generate signals corresponding to monitored glucose level in the bodily fluid; a glucose monitor operatively coupled to the glucose sensor to process the signals from the glucose sensor and to generate glucose measurement data; and a data processing device in signal communication with the glucose monitor to receive the glucose measurement data, the data processing device including: one or more processors; and a storage unit operatively coupled to the one or more processors and configured to store instructions which, when executed by the one or more processors, controls the one or more processors to perform meal start time determination for each one day time period, to determine a plurality of fasting metrics, each fasting metric corresponding to a respective one day time period, to determine an overall fasting metric, and to generate fasting glucose level information.

In an embodiment, the data processing device includes a data server located remotely from the glucose monitor. The data processing device may include a mobile telephone configured to receive the generated glucose measurement data from the glucose monitor.

In embodiments, the system may include an insulin delivery device in signal communication with the data processing device, the insulin delivery device configured to provide insulin delivery information to the data processing device, and further, wherein the data processing device is configured to retrieve from the storage unit a meal start time of day period, to identify an insulin delivery information within the meal start time of day period received from the insulin delivery device, to determine a potential meal start time within the meal start time of day period, to compare the insulin delivery information with the potential meal start time, and to set the meal start time as the determined potential meal start time when the insulin delivery information correlates with the potential meal start time based on the comparison.

A method of performing post-prandial glucose level information analysis includes performing meal start time determination for each one day time period; determining a post-prandial metric for each day based on the meal start time for the corresponding day; determining an overall post-prandial metric from the plurality of the post-prandial metric for each day; and generating a post-prandial glucose level information.

In embodiments, determining the post-prandial metric for each day includes retrieving glucose data for a first time period relative to the meal start time; determining a pre-meal glucose parameter from the retrieved glucose data for the first time period; retrieving glucose data for a second time period relative to the meal start time; determining a post-meal glucose parameter from the retrieved glucose data for the second time period; and determining a post-prandial glucose metric from the pre-meal and post-meal glucose parameters. The first time period may end before the beginning of the meal start time, and the second time period starts after the end of the meal start time. The pre-meal glucose parameter may be determined by applying a function to the retrieved glucose data for the first time period. The function may include one or more of a median, a mean, a standard deviation, an interquartile range, a minimum, or a maximum.

The post-meal glucose parameter may be determined by applying a function to the retrieved glucose data for the second time period. The function may include one or more of a median, a mean, a standard deviation, an interquartile range, a minimum, or a maximum.

In an embodiment, performing the meal start time determination includes: retrieving from a storage unit a meal start time of day period; retrieving an insulin delivery information within the meal start time of day period; determine a potential meal start time within the meal start time of day period; comparing the insulin delivery information with the potential meal start time; and setting the meal start time as the determined potential meal start time when the insulin delivery information correlates with the potential meal start time based on the comparison.

In an aspect, an apparatus for forming post-prandial glucose level information analysis comprises one or more processors; and a storage unit operatively coupled to the one or more processors and configured to store instructions which, when executed by the one or more processors, controls the one or more processors to perform meal start time determination for each one day time period, to determine a post-prandial metric for each day based on the meal start time for the corresponding day, to determine an overall post-prandial metric from the plurality of the post-prandial metric for each day, and to generate a post-prandial glucose level information.

In an embodiment, the or more processors executing the stored instructions to determine the post-prandial metric for each day may be configured to retrieve glucose data for a first time period relative to the meal start time, to determine a pre-meal glucose parameter from the retrieved glucose data for the first time period, to retrieve glucose data for a second time period relative to the meal start time, to determine a post-meal glucose parameter from the retrieved glucose data for the second time period, and to determine a post-prandial glucose metric from the pre-meal and post-meal glucose parameters. The first time period ends before the beginning of meal start time, and the second time period starts after the end of the meal start time. The pre-meal glucose parameter may be determined by applying a function to the retrieved glucose data for the first time period. The function may include one or more of a median, a mean, a standard deviation, an interquartile range, a minimum, or a maximum.

In an aspect, the post-meal glucose parameter may be determined by applying a function to the retrieved glucose data for the second time period. The function may include one or more of a median, a mean, a standard deviation, an interquartile range, a minimum, or a maximum.

A system for performing post-prandial glucose level information analysis, comprises: an in vivo glucose sensor having a portion positioned under a skin surface and in contact with bodily fluid and configured to generate signals corresponding to monitored glucose level in the bodily fluid; a glucose monitor operatively coupled to the glucose sensor to process the signals from the glucose sensor and to generate glucose measurement data; and a data processing device in signal communication with the glucose monitor to receive the glucose measurement data, the data processing device including: one or more processors; and a storage unit operatively coupled to the one or more processors and configured to store instructions which, when executed by the one or more processors, controls the one or more processors to perform meal start time determination for each one day time period, to determine a post-prandial metric for each day based on the meal start time for the corresponding day, to determine an overall post-prandial metric from the plurality of the post-prandial metric for each day, and to generate a post-prandial glucose level information.

In aspects, the data processing device determining the post-prandial metric for each day may be configured to retrieve glucose data for a first time period relative to the meal start time, to determine a pre-meal glucose parameter from the retrieved glucose data for the first time period, to retrieve glucose data for a second time period relative to the meal start time, to determine a post-meal glucose parameter from the retrieved glucose data for the second time period, and to determine a post-prandial glucose metric from the pre-meal and post-meal glucose parameters.

In an embodiment, the data processing device may include a data server located remotely from the glucose monitor.

In another embodiment, the data processing device may include a mobile telephone configured to receive the generated glucose measurement data from the glucose monitor.

In an aspect, the system includes an insulin delivery device in signal communication with the data processing device, the insulin delivery device configured to provide insulin delivery information to the data processing device, and further, wherein the data processing device performing the meal start time determination is configured to retrieve from the storage unit a meal start time of day period, to receive from the insulin delivery device the insulin delivery information within the meal start time of day period, to determine a potential meal start time within the meal start time of day period, to compare the insulin delivery information with the potential meal start time, and to set the meal start time as the determined potential meal start time when the insulin delivery information correlates with the potential meal start time based on the comparison.

In embodiments, the one or more processors executing the stored instructions to perform the meal start time determination may be configured to retrieve from the storage unit a meal start time of day period, to retrieve an insulin delivery information within the meal start time of day period, to determine a potential meal start time within the meal start time of day period, to compare the insulin delivery information with the potential meal start time, and to set the meal start time as the determined potential meal start time when the insulin delivery information correlates with the potential meal start time based on the comparison.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A system for diagnosing impaired glucose tolerance, the system comprising:
   an in vivo glucose sensor comprising a portion configured to be placed in fluid contact with a bodily fluid of a user under a skin surface to generate signals indicative of glucose levels;
   sensor electronics coupled to the in vivo glucose sensor and configured to be placed on the skin surface, wherein the sensor electronics are configured to communicate glucose data;
   one or more processors in communication with the sensor electronics; and
   one or more computer-readable non-transitory storage media comprising instructions that, when executed by the one or more processors, cause one or more components of the system to perform operations comprising:
      retrieving, from a storage unit, a meal start time of day period;
      identifying a delivery time within the meal start time of day period based on data received from an insulin delivery device;
      receiving glucose data collected by the in vivo glucose sensor during the meal start time of day period;
      determining a potential meal start time within the meal start time of day period using the glucose data;
      setting the meal start time as the potential meal start time when the delivery time correlates with the potential meal start time;
      determining a pre-meal glucose parameter based on the glucose data in a first predetermined period before the meal start time;
      determining a post-meal glucose parameter based on the glucose data in a second predetermined period following the meal start time;
      determining a postprandial glucose metric based on the pre-meal glucose parameter and the post-meal glucose parameter;
      determining diagnosis information indicating impaired glucose tolerance using the postprandial glucose metric; and
      outputting the diagnosis information on a user interface in communication with the one or more processors, wherein the diagnosis information comprises a median glucose level or a maximum glucose level based on the glucose data in the second predetermined period.

2. The system of claim 1, wherein the delivery time is associated with one of the following:
   an insulin delivery time; or
   a time associated with a meal start tag.

3. The system of claim 1, wherein the sensor electronics are configured to:
   process the signals indicative of the glucose levels in the bodily fluid; and
   generate the glucose data.

4. The system of claim 1, wherein:
   the glucose sensor comprises a plurality of electrodes;
   the plurality of electrodes comprises a working electrode; and an analyte-responsive enzyme or a mediator is bound to a polymer disposed on the working electrode.

5. The system of claim 1, wherein determining the potential meal start time within the meal start time of day period using the glucose data comprises identifying a beginning of a glucose level change in direction.

6. The system of claim 1, wherein the pre-meal glucose parameter comprises a median of the glucose data, and wherein the post-meal glucose parameter comprises a maximum glucose level of the glucose data.

7. The system of claim 6, wherein the postprandial glucose metric comprises a difference between the post-meal glucose parameter and the pre-meal glucose parameter.

8. One or more computer-readable non-transitory storage media embodying instructions that, when executed by a processor, cause the processor to perform operations comprising:

retrieving, from a storage unit, a meal start time of day period;

identifying a delivery time within the meal start time of day period based on data received from an insulin delivery device;

receiving glucose data collected during the meal start time of day period from sensor electronics placed on a skin surface of a user, wherein the sensor electronics are coupled to an in vivo glucose sensor comprising a portion placed in fluid contact with a bodily fluid of the user under the skin surface to generate signals indicative of glucose levels;

determining a potential meal start time within the meal start time of day period using the glucose data;

setting the meal start time as the potential meal start time when the delivery time correlates with the potential meal start time;

determining a pre-meal glucose parameter based on the glucose data in a first predetermined period before the meal start time;

determining a post-meal glucose parameter based on the glucose data in a second predetermined period following the meal start time;

determining a postprandial glucose metric based on the pre-meal glucose parameter and the post-meal glucose parameter;

determining diagnosis information indicating impaired glucose tolerance using the postprandial glucose metric; and outputting the diagnosis information on a user interface in communication with the processor, wherein the diagnosis information comprises a median glucose level or a maximum glucose level based on the glucose data in the second predetermined period.

9. The one or more computer-readable non-transitory storage media of claim 8, wherein the delivery time is associated with one of the following:

an insulin delivery time; or a time associated with a meal start tag.

10. The one or more computer-readable non-transitory storage media of claim 8, wherein determining the potential meal start time within the meal start time of day period using the glucose data comprises identifying a beginning of a glucose level change in direction.

11. The one or more computer-readable non-transitory storage media of claim 8, wherein the pre-meal glucose parameter comprises a median of the glucose data, and wherein the post-meal glucose parameter comprises a maximum glucose level of the glucose data.

12. The one or more computer-readable non-transitory storage media of claim 11, wherein the postprandial glucose metric comprises a difference between the post-meal glucose parameter and the pre-meal glucose parameter.

13. A method for diagnosing impaired glucose tolerance, the method comprising:

retrieving, from a storage unit, a meal start time of day period;

identifying a delivery time within the meal start time of day period based on data received from an insulin delivery device;

receiving glucose data collected during the meal start time of day period from sensor electronics arranged on a skin surface of a user, wherein the sensor electronics are coupled to an in vivo glucose sensor comprising a portion placed in fluid contact with a bodily fluid of the user under the skin surface to generate signals indicative of glucose levels;

determining a potential meal start time within the meal start time of day period using the glucose data;

setting the meal start time as the potential meal start time when the delivery time correlates with the potential meal start time;

determining a pre-meal glucose parameter based on the glucose data in a first predetermined period before the meal start time;

determining a post-meal glucose parameter based on the glucose data in a second predetermined period following the meal start time;

determining a postprandial glucose metric based on the pre-meal glucose parameter and the post-meal glucose parameter;

determining diagnosis information indicating impaired glucose tolerance using the postprandial glucose metric; and outputting the diagnosis information on a user interface, wherein the diagnosis information comprises a median glucose level or a maximum glucose level based on the glucose data in the second predetermined period.

14. The method of claim 13, wherein the delivery time is associated with one of the following:

an insulin delivery time; or a time associated with a meal start tag.

15. The method of claim 13, wherein determining the potential meal start time within the meal start time of day period using the glucose data comprises identifying a beginning of a glucose level change in direction.

16. The method of claim 13, wherein the pre-meal glucose parameter comprises a median of the glucose data, and wherein the post-meal glucose parameter comprises a maximum glucose level of the glucose data.

17. The method of claim 16, wherein the postprandial glucose metric comprises a difference between the post-meal glucose parameter and the pre-meal glucose parameter.

* * * * *